United States Patent [19]

Gschwind et al.

[11] Patent Number: 5,741,067
[45] Date of Patent: Apr. 21, 1998

[54] METHOD OF PREDICTING THE FORMATION OF WATER CONDENSATION

[75] Inventors: Michel Gschwind, Plascassier; Pascal Ancey, Grasse, both of France

[73] Assignee: Imra Europe SA, Valbonne, France

[21] Appl. No.: 620,532

[22] Filed: Mar. 25, 1996

[30] Foreign Application Priority Data

Mar. 23, 1995 [FR] France ................... 95 03413

[51] Int. Cl.[6] ........................................ G01N 25/12
[52] U.S. Cl. ........................ 374/16; 374/45; 374/28
[58] Field of Search .......................... 374/5, 11, 16, 374/20, 21, 27, 28, 45

[56] References Cited

U.S. PATENT DOCUMENTS

| | | | |
|---|---|---|---|
| 3,396,574 | 8/1968 | Hanlein et al. | 374/28 |
| 4,240,284 | 12/1980 | Nguyen | 374/20 |
| 4,677,416 | 6/1987 | Nishimoto et al. | 374/28 |
| 4,981,369 | 1/1991 | Kumada et al. | 374/16 |
| 5,364,185 | 11/1994 | VanZandt et al. | 374/28 |
| 5,568,977 | 10/1996 | Gschwind et al. | 374/28 |

FOREIGN PATENT DOCUMENTS

| | | |
|---|---|---|
| 0 613 000 A1 | 8/1994 | European Pat. Off. . |
| 2 623 909 | 6/1989 | France . |

Primary Examiner—G. Bradley Bennett
Attorney, Agent, or Firm—Oliff & Berridge

[57] ABSTRACT

A method of predicting the formation of water condensation on a surface in contact with humid air includes the steps of placing on the surface an element that adopts initially a temperature approximately equal to a temperature of the surface. The element is thermally cycled. Each cycle includes a cooling phase and a heating phase. The cooling phase includes first and second steps. Electric current is supplied to a cooling mechanism in the first step of the cooling phase to decrease the temperature of the element to below the temperature of the surface. An electric current is supplied to the cooling mechanism in the second step of the cooling phase to further decrease the temperature of the element. The current of the first step is greater than the current of the second step, such that the temperature of the element decreases more rapidly in the first step than in the second step. The formation of water condensation on the surface is predicted based upon the formation of water condensation on the element.

9 Claims, 3 Drawing Sheets

METHOD OF PREDICTING THE FORMATION OF WATER CONDENSATION

BACKGROUND OF THE INVENTION

1. Field of the Invention

The present invention relates to a method of predicting the formation of water condensation on a surface that is in contact with humid air.

2. Description of the Related Art

A conventional method of predicting the formation of water condensation is disclosed in FR-A-2 702 049. This process includes placing a sensitive element on a surface. The surface initially has approximately the same temperature as the element. A heating mechanism increases the temperature of the element to a temperature greater than that of the surface in a preliminary heating step. A cooling mechanism having the same thermal capacity as the heating mechanism decreases the temperature of the element to below the temperature of the surface in a cooling step. The ratio of the duration of the preliminary heating step to the temperature increase during the heating step is compared with the ratio of the duration of the cooling phase to the temperature decrease during the cooling step. A significant difference between the two ratios indicates that water condensation may form on the surface.

The conventional process predicts the formation of water condensation on a surface based upon the amplitude of thermal oscillations. However, the effectiveness of the conventional process is limited because of the low frequency of thermal oscillations of the sensitive element. To produce thermal oscillations, the element is provided with heating and cooling energy. More energy must be provide to increase the thermal amplitude of the oscillations. A high capacity heating and cooling mechanism can provide this energy over a very short period of time. Alternatively, a low capacity heating and cooling mechanism can provide this energy over a long period of time.

Each of these alternatives has disadvantages. The high capacity heating and cooling mechanism consumes too much energy and is not accurate. Specifically, the energy supplied to the element may be too high compared to the energy required to condense water. The temporal disruption generated by condensation of the first droplets is negligible. The delay in the cooling phase caused by the negligible disruption is, therefore, too small to be detected.

The low capacity heating and cooling mechanism is also not accurate. If the energy supplied to the element is too low, the duration of the heating and cooling steps is lengthened. The lengthening of the heating and cooling steps delays the prediction of the formation of water condensation on a surface.

SUMMARY OF THE INVENTION

It is therefore, an object of the present invention to provide an accurate and reliable method of predicting the formation of water condensation. It is also an object of the invention to provide for the early prediction of the formation of water condensation.

The present invention is a method of predicting the formation of water condensation on a surface that is in contact with humid air. A sensitive element is placed on the surface. The element initially has approximately the same temperature as the surface. Heating and cooling mechanisms provide thermal cycles. Each thermal cycle includes a heating phase and a cooling phase. The heating mechanism heats the element in the heating phase. The cooling mechanism cools the element in the cooling phase. The cooling phase of each cycle is performed in two consecutive steps. In the first step, high power is supplied to the cooling mechanism to rapidly decrease the temperature of the element relative to the temperature of the surface. In the second step, low power is supplied to the cooling mechanism to slowly reduce the temperature of the element. Low power continues to be supplied to the cooling mechanism until the end of the cooling step.

The high power of the first step affords relatively short thermal cycles. The short thermal cycles provide for the early prediction of the formation of water condensation. The low power of the second step is closer to the amount of energy required to condense water. The lower power highlights the temporal disruption generated by the condensation of water droplets, and thus accurately predicts the formation of water condensation.

In the preferred embodiment of the invention, the temperature of the element is measured during the cooling phase of each cycle. The cooling phase is interrupted when the element reaches a predetermined low temperature. The temperature of the element is also measured during the heating phase of each cycle. The heating phase is interrupted when the element reaches a predetermined high temperature. This method is simple to implement; however, it requires the use of a mechanism for accurately measuring the temperature of the element.

The duration of the thermal cycles is monitored. A lengthening of the thermal cycles indicates the formation of water condensation on the element. The formation of water condensation on the element indicates the imminent formation of water condensation on the surface.

Alternatively, the heating phase can continue for a fixed duration. For example, the length of the heating phase can equal the duration of the cooling phase of the same cycle. The heating phase can also be set to continue for a period of time equal to the average duration of multiple cooling phases.

In the alternative embodiment, each heating phase is performed in two consecutive steps. The duration of the first step is equal to the duration of the first step of the cooling phase. The power supplied to the heating mechanism in the first step is approximately equal to the power supplied to the cooling mechanism during the first step of the cooling phase. The duration of the second step is equal to the duration of the second step of the cooling phase. The power supplied to the heating mechanism in the second step of the heating phase is approximately equal to the power supplied to the cooling mechanism during the second step of the cooling phase.

The formation of water condensation is predicted by comparing the ratio of the duration of the heating phase and the temperature increase during the heating phase with the ratio of the duration of the cooling phase and the temperature decrease during the cooling phase. A significant difference between the two ratios indicates the formation of water condensation on the element. The formation of water condensation on the element indicates the imminent formation of water condensation on the surface.

In another alternative embodiment of the invention, the energy supplied to cool the element during the cooling phase of the first cycle is measured and recorded. The energy supplied to heat and cool the element during subsequent heating and cooling phases is measured. The subsequent heating and cooling phases are interrupted when the energy supplied to the element is equal to the previously recorded energy.

In still another alternative embodiment, the energy supplied to cool the element during the first cooling phase of the first cycle is be compared to a stored value. The method includes a step of determining whether or not the difference between the energy of the first cooling phase of the first cycle and the stored value is minimal. If the difference is minimal, the new measured value is recorded and used for subsequent implementation in the process. However, a large difference indicates either a malfunction or the presence of water condensation on the element during the first thermal cycle.

This embodiment can be combined with the preferred embodiment of the invention. The energy is only measured during the heating phases. The duration of the cooling phases is determined by measuring the temperature of the element during cooling, and comparing the measured temperature with a predetermined lower temperature.

Other objects, advantages and salient features of the invention will become apparent from the detailed description taken in conjunction with the annexed drawings, which disclose preferred embodiments of the invention.

BRIEF DESCRIPTION OF THE DRAWINGS

The invention will be described with reference to the following drawings in which like reference numerals refer to like elements and wherein.

DETAILED DESCRIPTION OF THE PREFERRED EMBODIMENT

Figure 1:
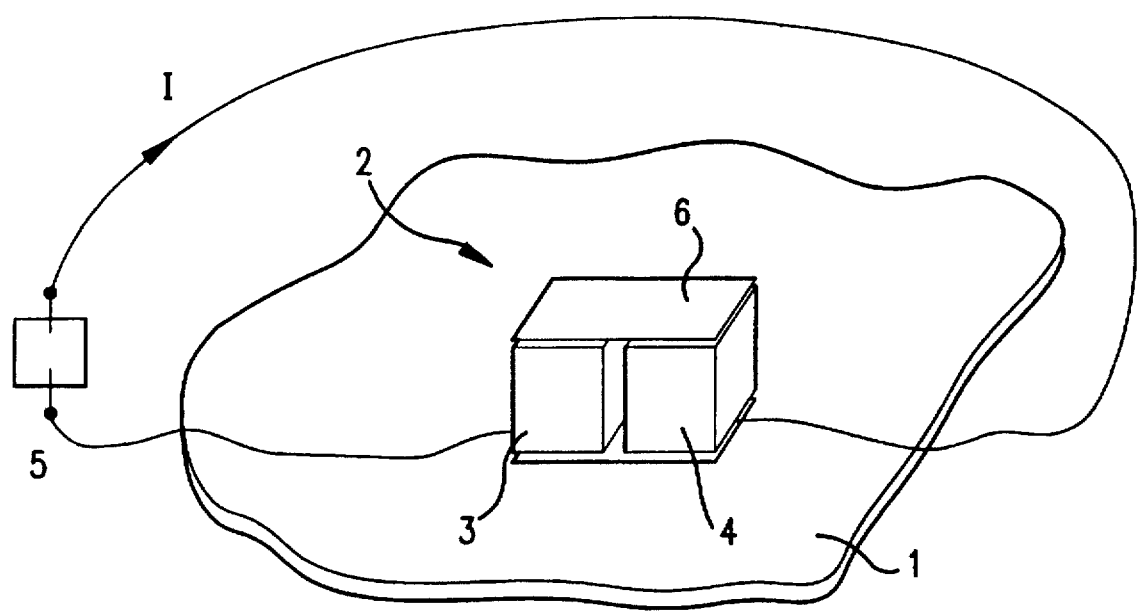
FIG. 1 is a perspective view showing apparatus for implementing a method of predicting the formation of water condensation on a surface in accordance with the preferred embodiment of the invention.

FIG. 1 is a perspective view showing apparatus for implementing a method of predicting the formation of water condensation on a surface in accordance with the preferred embodiment of the invention. The apparatus includes a Peltier effect module 2. The module 2 includes two semi-conductor elements 3 and 4, doped N and P respectively. The elements 3 and 4 are electrically connected in series. A current generator 5 supplies power to the elements 3 and 4.

A plate 6 is formed of a thermally conductive material. The plate 6 links upper ends of the semi-conductor elements 3 and 4. The plate 6 constitutes a thermally sensitive element. The plate 6 is subject to thermal oscillations when current I supplied to the elements 3 and 4 is varied.

When the Peltier effect module 2 is not supplied with any current, the plate 6 adopts the temperature of the surface 1. Both ends of each semi-conductor element 3 and 4 have the same temperature. The Seebeck voltage at the Peltier effect module 2 is zero.

In the preferred embodiment of the invention, the thermal amplitude of the cycles is determined by measuring the Seebeck voltage $U_p$. The Seebeck voltage $U_p$ indicates whether or not there is a difference in temperature $\pm \Delta T$ between the plate 6 and the surface 1.

A current +I is supplied to the Peltier effect module 2 to increase the temperature of the plate 6. The increased temperature of the plate 6 equals $T+\Delta T$, wherein T is the temperature of the surface 1. The voltage U of terminals of the module 2 is measured when the current is supplied. The Seebeck voltage $U_p$ is determined by subtracting a resistance component $U_r$ from the measured voltage, i.e., $U_p = U - U_r$.

The temperature of the plate 6 is equal to $T+\Delta T$ when the Seebeck voltage has reached a value that corresponds to a temperature difference $\Delta T$ between the two ends of the semi-conductor elements 3 and 4. This calculation is accurate when the change in temperature of the surface 2, due to thermal disturbance created by the Peltier effect, is negligible.

The plate 6 is similarly cooled to a temperature $T-\Delta T$.

Figure 2:
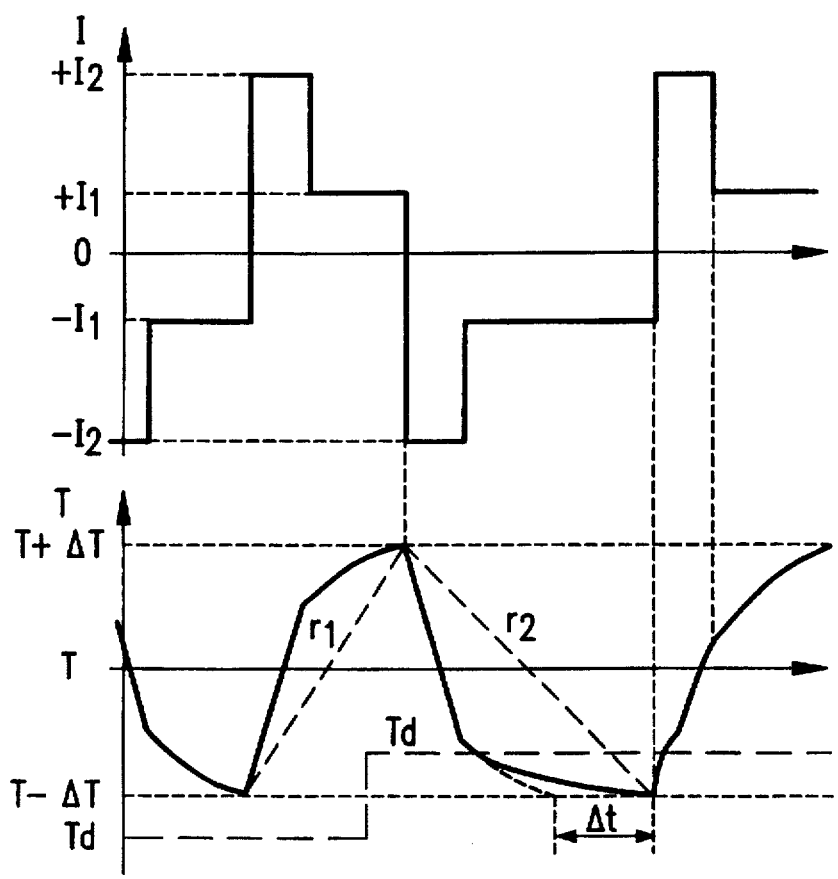
FIG. 2 is a graphic representation of current supplied to the apparatus of FIG. 1 and the temperature of an element as a function of the current.

FIG. 2 is a graphic representation of current supplied to the apparatus of FIG. 1, and the temperature of an element as a function of the current. Specifically, FIG. 2 shows the current supplied to the Peltier effect module 2 as a function of time. FIG. 2 also shows the temperature of the plate 6 as a function of time, and the current supplied to the Peltier effect module 2.

The heating and cooling phases are each divided into two steps. The current $I_2$ is strong in the first step. The current $I_1$ is weak in the second step. FIG. 2 shows that the temperature increases and decreases rapidly when the current is strong, and changes more slowly when the current is weak.

Water condenses on the plate 6 when $T-\Delta T$ is less than the dew point temperature $T_d$ during the second step of the cooling phase. The water condensation causes a non-negligible delay $\Delta t$ in the cooling phase based upon the slow change of temperature of the plate 6. The formation of water condensation on the surface 1 is predicted by measuring the delay $\Delta T$ of the cooling phase.

FIG. 2 shows the heating phases divided into two steps. It is also possible to detect condensation on the upper plate by comparing the absolute values of the slopes $r_1$ and $r_2$ of the heating and cooling phases.

Figure 3:
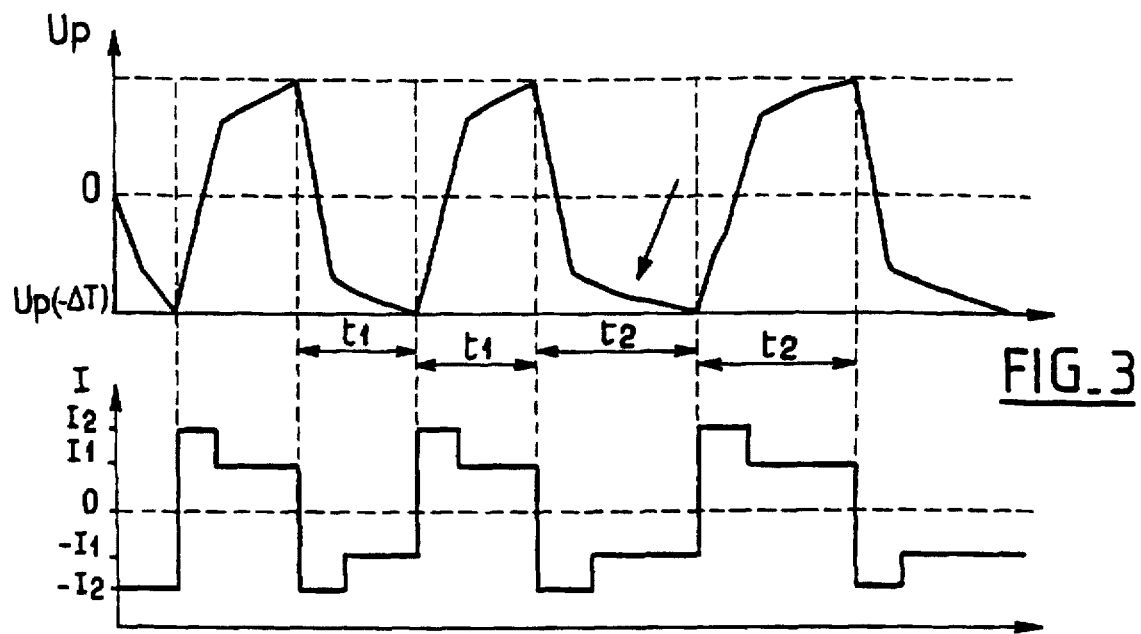
FIG. 3 is a graphic representation of current supplied to apparatus of an alternative embodiment of the invention, and the temperature of an element as a function of the current.

FIG. 3 is a graphic representation of current supplied to an apparatus of an alternative embodiment of the invention, and the temperature of an element as a function of the current. In the embodiment shown in FIG. 3, the temperature of the plate 6 is only measured during the cooling phases.

The Seebeck voltage at terminals of the Peltier effect module 2 is measured. The cooling phase is interrupted when there is a difference $\Delta T$ between the temperature T of the surface 1 and the temperature $T-\Delta T$ of the plate 6.

The duration $t_i$ of each cooling phase is measured during each thermal cycle. The duration of the heating phase of the same cycle is set at the same duration $t_i$.

When condensation appears on the plate 6, as evidenced by a dip during the second cycle, the duration $t_2$ of the cooling phase increases. Consequently, the next heating phase continues for the increased period of time $t_2$. The thermal cycle is, thus, extended to a period time equal to $2t2$. The extended thermal cycle provides for the accurate prediction of the formation of condensation.

Figure 4:
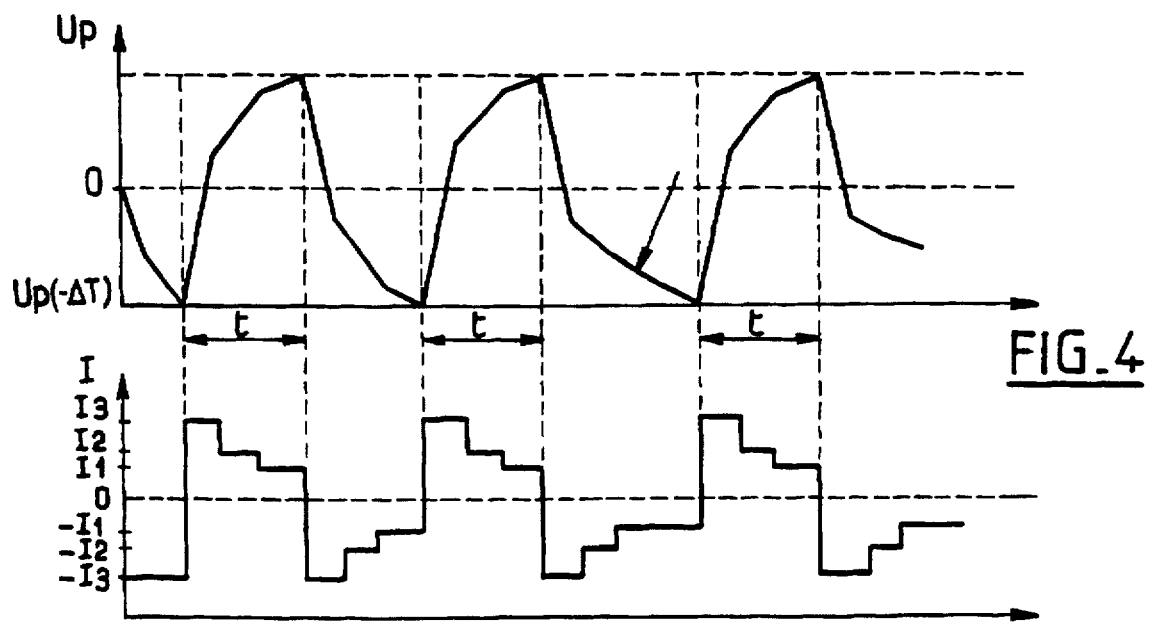
FIG. 4 is graphic representation of current supplied to apparatus of another embodiment of the invention, and the temperature of an element as a function of the current.

FIG. 4 is a graphic representation of current supplied to apparatus of another embodiment of the invention, and the temperature of an element as a function of the current. In the embodiment shown in FIG. 4, the duration t of each heating phase is equal to the average duration of the cooling phases of multiple cycles N. The number of cycles N is preferably between 1 and 10.

The duration t is fixed. Therefore, water condensing on the plate 6, as indicated by a dip during the second cycle, prevents the plate 6 from reaching its maximum temperature T+ΔT. Instead, the plate 6 only reaches a lower temperature because of the energy required during heating to evaporate the water, e.g. latent heat. Water condensation forms earlier during the cooling phase of the next cycle. This phenomenon extends the duration of each cycle. The extended thermal cycle provides for the accurate prediction of the formation of condensation on the surface 1.

Figure 5:
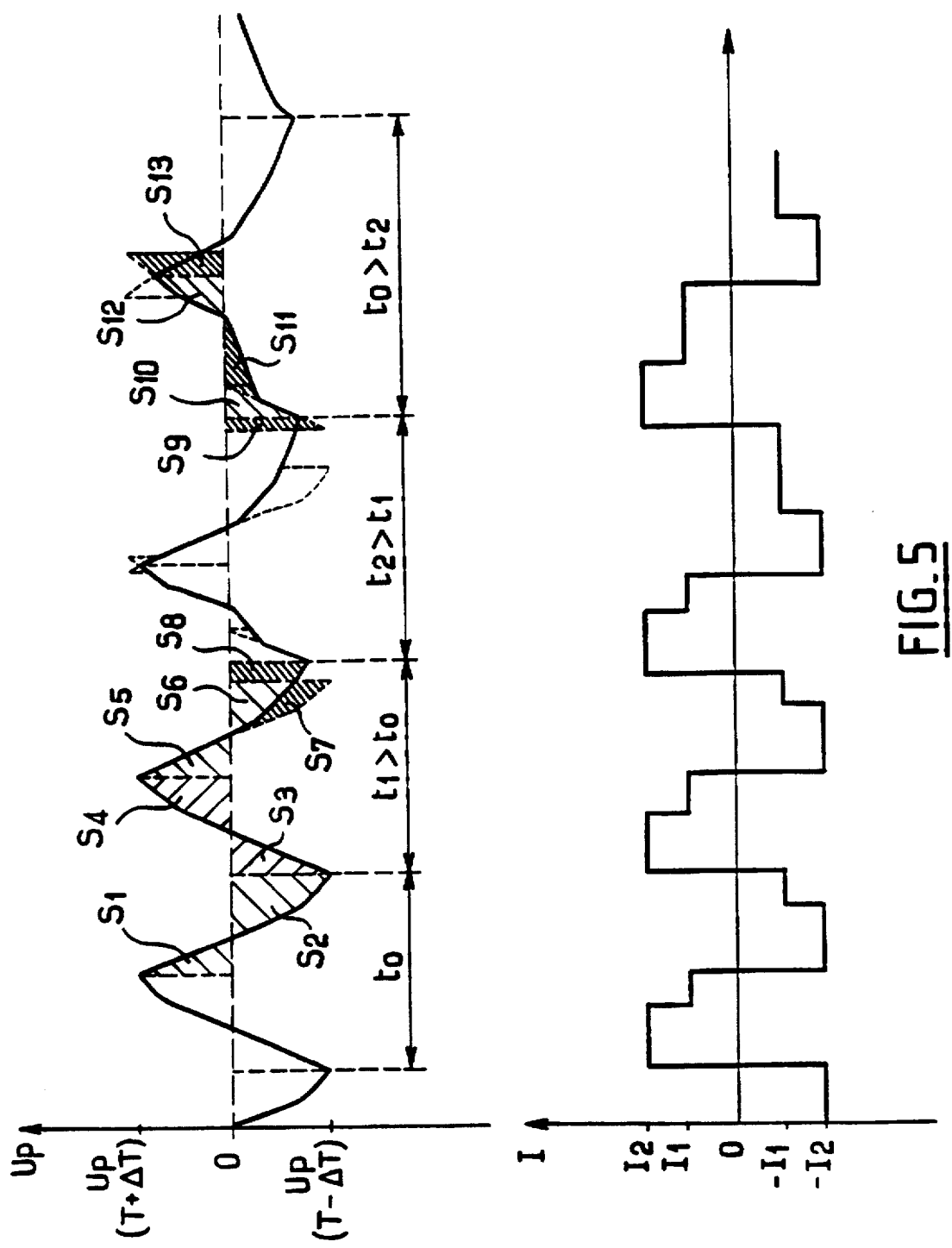
FIG. 5 is a graphic representation of current supplied to apparatus of yet another embodiment of the invention, and the temperature of an element as a function of the current.

FIG. 5 is a graphic representation of current supplied to apparatus of yet another embodiment of the invention, and the temperature of an element as a function of the current. In the embodiment shown in FIG. 5, the heating and cooling phases are divided into three steps, instead of just two as in the previously described embodiments. The three steps provide for more gradual changes in the current supplied to the module 2, especially during cooling. The gradual changes of the current provide greater sensitivity for detecting condensed water on the element.

The energy supplied to the plate 6 is measured time during the first cooling phase. This energy is represented on the drawings as surfaces $S_1$ and $S_2$. The energy supplied in the first cooling phase is recorded at the beginning of the first cycle. Subsequent heating and cooling phases are set so that the energy supplied to the plate 6 is equal to the energy recorded.

Therefore, the energy supplied to the plate 6 in the first heating cycle is the same as the recorded energy supplied to the plate 6 in the first cooling cycle. The magnitude of the recorded energy is shown in FIG. 5, wherein surfaces $S_3$ and $S_4$ are equal in area to surfaces $S_1$ and $S_2$ respectively.

The plate 6 reaches its high and low temperature set points when there is no condensation. However, condensation formed on the plate 6 prevents it from reaching its high and low set points. Energy is supplied during the cooling phase until it equals the recorded limit. FIG. 5 shows the energy balance wherein: $S_5=S_1$ and $S_6+S_8=S_2$, given that $S_8=S_7$.

Subsequent heating and cooling phases are also prolonged. FIG. 5 shows that the energy supplied during heating is equal to the recorded energy in the fourth cycle wherein: $S_{10}+S_{11}+S_{12}=S_1+S_2$, given that $S_{11}=S_9+S_{13}$. The thermal amplitude of the cycles is decreased, whereas the time period is increased. The formation of water condensation on the surface is predicted by monitoring changes in the duration of the thermal cycles.

Various changes can be made to the described embodiments. For example, changes in the Seebeck voltage can be monitored at terminals of the Peltier effect module 2. A decrease in the thermal amplitude of the cycles can be observed based upon changes in the Seebeck voltage. The formation of water condensation on the surface is predicted based upon a decrease in the thermal amplitude.

Also, the current supplied to the module 2 in the cooling phase can be reduced continuously. This continuous reduction of current is equivalent to dividing the cooling phase into an infinite number of steps.

Still other modifications, which will occur to persons skilled in the art, may be made without departing from the scope of the invention as defined in the following claims.

What is claimed is:

1. A method of predicting the formation of water condensation on a surface in contact with humid air, comprising the steps of:

placing on the surface an element that adopts initially a temperature approximately equal to a temperature of the surface;

thermally cycling the element, each cycle including a cooling phase and a heating phase, wherein the cooling phase includes first and second consecutive steps;

supplying an electric current to a cooling mechanism in the first step of the cooling phase to decrease the temperature of the element to below the temperature of the surface; and supplying an electric current to the cooling mechanism in the second step of the cooling phase to further decrease the temperature of the element, wherein the current of the first step is greater than the current of the second step such that the temperature of the element decreases more rapidly in the first step than in the second step;

whereby the formation of water condensation on the surface is predicted based upon the formation of water condensation on the element.

2. A method according to the steps of claim 1, further comprising the steps of measuring the temperature of the element during the cooling phase of each cycle, and interrupting the cooling phase when the temperature of the element reaches a predetermined low temperature.

3. A method according to the steps of claim 2, further comprising the steps of measuring the temperature of the element during the heating phase of each cycle, and interrupting the heating phase when the temperature of the element reaches a predetermined high temperature.

4. A method according to the steps of claim 2, further comprising the step of interrupting the heating phase such that the duration of the heating phase of a cycle is equal to the duration of the cooling phase of the same cycle.

5. A method according to the steps of claim 2, further comprising the step of interrupting the heating phase such that the duration of the heating phase is equal to an average duration of multiple cooling phases.

6. A method according to the steps of claim 2, further comprising the steps of monitoring the duration of multiple thermal cycles and predicting the formation of water on the surface based upon an increased duration of the thermal cycles.

7. A method according to the steps of claim 2, further comprising the step of supplying current to the heating mechanism in two steps in the heating phase, wherein the first step of the heating phase has a duration equal to that of the first step of the cooling phase, the current supplied to the heating mechanism during the first step of the heating phase is approximately equal to the current supplied to the cooling mechanism during the first step of the cooling phase, and the current supplied to the heating mechanism in the second step of the heating phase is approximately equal to the current supplied to the cooling mechanism during the second step of the cooling phase; the step of comparing the ratio of the duration of the heating phase and the temperature increase during the heating phase with the ratio of the duration of the cooling phase to the temperature decrease during cooling; and the step of predicting the formation of water condensation on the surface based upon the step of comparing.

8. A process according to the steps of claim 1, further comprising the steps of measuring and recording the current supplied in the cooling phase of a first cycle, measuring the current supplied in the heating and cooling phases of subsequent cycles, and interrupting subsequent heating cooling phases when the current supplied to the heating and cooling mechanisms equals the recorded current.

9. A process according to the steps of claim 1, further comprising the step interrupting the cooling phase by measuring the temperature of the element during the cooling phase and comparing the measured temperature with a predetermined low temperature.

* * * * *